United States Patent
Kovesdi et al.

(10) Patent No.: US 6,472,176 B2
(45) Date of Patent: Oct. 29, 2002

(54) POLYNUCLEOTIDE ENCODING CHIMERIC PROTEIN AND RELATED VECTOR, CELL, AND METHOD OF EXPRESSION THEREOF

(75) Inventors: Imre Kovesdi, Rockville; Joseph T. Bruder, Ijamsville, both of MD (US)

(73) Assignee: GenVec, Inc., Gaithersburg, MD (US)

( * ) Notice: Subject to any disclaimer, the term of this patent is extended or adjusted under 35 U.S.C. 154(b) by 0 days.

(21) Appl. No.: 09/736,743

(22) Filed: Dec. 14, 2000

(65) Prior Publication Data

US 2002/0110869 A1 Aug. 15, 2002

(51) Int. Cl.[7] ...................... C12P 21/00; C12N 15/861; C12N 15/86; C12N 5/10; C07H 21/04

(52) U.S. Cl. ................... 435/69.1; 435/320.1; 435/69.7; 435/69.8; 435/455; 435/325; 536/23.1; 536/23.2; 536/23.4; 536/23.5; 536/23.7; 536/24.1

(58) Field of Search ...................... 435/320.1, 69.1, 435/69.7, 69.8, 455, 325; 536/23.1, 23.2, 23.4, 23.5, 23.7, 24.1

(56) References Cited

U.S. PATENT DOCUMENTS

| 5,580,859 A | 12/1996 | Felgner et al. | |
|---|---|---|---|
| 5,801,030 A | 9/1998 | McVey et al. | |
| 5,804,604 A | 9/1998 | Frankel et al. | |
| 5,888,762 A | 3/1999 | Joliot et al. | |
| 6,280,989 B1 * | 8/2001 | Kapitonov et al. | 435/193 |
| 6,281,413 B1 * | 8/2001 | Kramer et al. | 800/302 |

FOREIGN PATENT DOCUMENTS

WO    WO 99/16884 A1    4/1999

OTHER PUBLICATIONS

Aullo et al., *The EMBO Journal*, 12 (3), 921–931 (Mar. 1993).
Bandara et al., *Nature Biotechnology*, 15, 896–901 (Sep. 1997).
Chatelin et al., *Mechanisms of Development*, 55, 111–117 (Apr. 1996).
Cress et al., *Journal of Virology*, 68 (7), 4212–4219 (Jul. 1994).
Derer et al., *Journal of Molecular Medicine*, 77, 609–613 (Aug. 1999).
Derossi et al., *Journal of Biological Chemistry*, 269 (14), 10444–10450 (Apr. 1994).
Derossi et al., *Trends in Cell Biology*, 8, 84–87 (Feb. 1998).
Elliott et al., *Gene Therapy*, 6, 149–151 (Jan. 1999).
Fawell et al., *PNAS USA*, 91 664–668 (Jan. 1994).
Fueyo et al., *Nature Medicine*, 4 (6), 685–690 (Jun. 1998).
Goldstein et al., *Journal of Bacteriology*, 172 (3), 1225–1231 (Mar. 1990).
Hall et al., *The Journal of Biological Chemistry*, 265 (32), 19996–19999 (Nov. 1990).
Hawiger, *Current Opinion in Immunology*, 9, 189–194 (Apr. 1997).
He et al., *Nature*, 373, 721–724 (Feb. 1995).
Inoue et al., *Annals of Microbiology*, 133 A, 257–259 (Mar./Apr. 1982).
Izard et al., *Molecular Microbiology*, 13 (5), 765–773 (Sep. 1994).
Joliot et al., *Current Biology*, 8, 856–863 (Jul. 1998).
Joliot et al., *Development*, 124, 1865–1875 (May 1997).
Ladunga, *Current Opinion in Biotechnology*, 11, 13–18 (Feb. 2000).
Mann et al., *The EMBO Journal*, 10 (7), 1733–1739 (Jul. 1991).
Oess et al., *Gene Therapy*, 7, 750–758 (May 2000).
Phelan et al., *Nature Biotechnology*, 18, 440–443 (May 1998).
Prochiantz et al., *BioEssays*, 17 (1), 39–44 (Jan. 1995).
Prochianz, *Annals New York Academy of Sciences*, 886, 179–179 (Nov. 1999).
Prochianz, *Current Opinion in Neurobiology*, 6, 629–634 (Oct. 1996).
Schwarze et al., *Trends in Cell Biology*, 10, 290–295 (Jul. 2000).
Vivés et al., *The Journal of Biological Chemistry*, 272 (25), 16010–16017 (Jun. 1997).
Yao et al., *Human Gene Therapy*, 9, 1939–1950, (Sep. 1998).
Zheng et al., *Nature Neuroscience*, 3 (6), 580–586 (Jun. 2000).

\* cited by examiner

*Primary Examiner*—David Guzo
(74) *Attorney, Agent, or Firm*—Leydig, Voit & Mayer, Ltd.

(57) ABSTRACT

The invention pertains to a polynucleotide encoding a chimeric protein comprising an endoplasmic reticulum localization signal peptide, a transport moiety, and a moiety of interest, wherein the endoplasmic reticulum localization signal peptide, the transport moiety, and the moiety of interest are operably linked with each other, a vector comprising the polynucleotide, a cell comprising such a vector, and a method of expressing a protein comprising the transport moiety and the moiety of interest.

25 Claims, No Drawings

POLYNUCLEOTIDE ENCODING CHIMERIC PROTEIN AND RELATED VECTOR, CELL, AND METHOD OF EXPRESSION THEREOF

TECHNICAL FIELD OF THE INVENTION

The invention generally pertains to a polynucleotide that encodes a chimeric protein and related vectors, cells, and methods of expression thereof.

BACKGROUND OF THE INVENTION

The introduction of nucleotides, peptides, and small molecules into target cells and tissues is being developed as a therapeutic approach to a wide-range of diseases. The viability of this therapeutic approach has increased with the increased understanding of the molecular biology of cell division and differentiation, the identification of disease mechanisms, and the ability to develop high-throughput screens for agonists and antagonists of particular targets. A problem remains, however, which is inherent to all aspects of gene therapy. Namely, there continue to exist major hurdles for delivering therapeutic peptides and/or genes encoding therapeutic peptides to a sufficient number of target cells, such that the desired phenotypic response is elicited.

A wide variety of delivery methods has been proposed, including microinjection, scrape loading, electroporation, liposomes, bacterial toxins, and receptor-mediated endocytosis. Most of these methods, however, are inefficient and can cause appreciable cell death. Recently, it has been observed that the human immunodeficiency virus transcriptional activation protein (HIV TAT), the herpes simplex viral protein 22 (HSV VP22), and similar proteins possess the ability to enter numerous cell types when added exogenously to cells in vitro. Investigators also have discovered that these select proteins have the ability to carry nucleotides, small molecules, and/or other peptides which are bound to these proteins into target cells with high efficiency and, therefore, act as transport proteins.

Despite the potential of these transport proteins in aiding in the delivery of therapeutic agents, there still exist drawbacks, which limit the feasibility of this delivery approach. In particular, the preparation and purification of a desired therapeutic polypeptide comprising both a transport protein and a therapeutic agent can be both time-consuming and expensive. Furthermore, when these therapeutic polypeptides are administered in vivo to an organism, the therapeutic polypeptides are susceptible to proteolytic attack and can initiate an undesired, and potentially harmful, immune response by the treated organism. Consequently, delivery methods utilizing transport proteins can lead to less than desired stability in vivo and can actually be deleterious to the treated organism, if, indeed, an immune reaction is provoked.

Accordingly, there remains a need for an improved method of delivering therapeutic agents and other agents of interest in vivo to target cells. The invention seeks to provide such a method and agents for use therein. These and other objects and advantages of the invention will be apparent from the description of the invention provided herein.

BRIEF SUMMARY OF THE INVENTION

The invention provides a polynucleotide encoding a chimeric protein comprising an endoplasmic reticulum (ER) localization signal peptide, a transport moiety, and a moiety of interest, wherein the ER localization signal peptide, the transport moiety, and the moiety of interest are operably linked with each other. The invention further provides a vector comprising the polynucleotide, a cell comprising such a vector, and a method of expressing a protein comprising the transport moiety and the moiety of interest.

DETAILED DESCRIPTION OF THE INVENTION

The invention provides a polynucleotide encoding a chimeric protein comprising an endoplasmic reticulum (ER) localization signal peptide, a transport moiety, and a moiety of interest. The ER localization signal peptide, the transport moiety, and the moiety of interest are operably linked with each other. As discussed below, the polynucleotide can (but need not) contain additional elements which do or do not affect the performance (e.g., expression or therapeutic effect) of the polynucleotide when utilized in vitro, in vivo, and/or ex vivo. Thus, the polynucleotide can encode a chimeric protein that comprises, consists essentially of, or consists of the ER localization signal peptide, the transport moiety, the moiety of interest, and optionally a nuclear localization signal and/or regulatory elements such as one or more promoters. Moreover, the polynucleotide of the invention preferably exists in an isolated and purified form.

The polynucleotide can be used to produce the chimeric protein and, in turn, a protein comprising the transport moiety and the moiety of interest but without the ER localization signal peptide. In particular, a vector can comprise the polynucleotide, and a cell can be contacted with the vector such that the polynucleotide enters the cell and is expressed to produce the chimeric protein, the ER localization signal peptide is cleaved from the chimeric protein, and a protein comprising the transport moiety and the moiety of interest is secreted from the cell. The protein secreted from the cell can be internalized by a different cell, and the protein can exert an effect, e.g., a therapeutic effect, on the different cell. In this manner, the invention provides a method of producing a protein containing a moiety of interest in a cell and secreting that protein containing a moiety of interest from the cell. As a result, the invention is particularly useful where that moiety of interest is not normally secreted by the cell or is normally secreted by the cell in a relatively low (i.e., less than desired) quantity. The invention further allows for the internalizing of that same protein containing a moiety of interest into a different cell, which is particularly useful where that moiety of interest is not normally internalized by the different cell or is normally internalized by the different cell in a relatively low (i.e., less than desired) quantity.

The ER localization signal peptide functions to direct an actively-expressing (i.e., translating) ribosome of a cell with which the polynucleotide is contacted (i.e., the "primary cell") to the membrane of the ER. In particular, when a ribosome in the primary cell completes the translation of the portion of the polynucleotide encoding the ER localization signal peptide, the ER localization signal peptide directs the migration of the actively-expressing ribosome to the ER membrane, prior to completion of the translation event. The ER localization signal peptide then binds to a receptor on the ER membrane (e.g., a signal-recognition particle (SRP) receptor), and translation of the chimeric protein proceeds, with the chimeric protein being translocated across the ER membrane through a translocator pore into the lumen of the ER without making any (or substantially any) contact with the cytosol of the primary cell. Once in the lumen of the ER, the ER localization signal peptide of the chimeric protein is cleaved off by a signal peptidase, and the remainder of the chimeric protein (i.e., the protein comprising the transport moiety and the moiety of interest) is targeted for secretion by the primary cell via a secretory vesicle, secretory granule, or dense core vesicle, and eventually secreted from the cell (see Alberts et al., *Molecular Biology of the Cell*, 3$^{rd}$ ed., 578–589 (1994)).

The lack of substantial contact (e.g., no contact) between the chimeric protein encoded by the polynucleotide and the cytosol of the primary cell can be of great significance, for example, when the moiety of interest of the chimeric protein is an apoptotic moiety, which could cause cell death in the primary cell if it is released into the cytosol. By incorporating an ER localization signal peptide into the polynucleotide, it is possible to increase the likelihood of survival of the primary cell and, therefore, increase the secretion potential of the protein comprising the transport moiety and the moiety of interest from the primary cell.

The ER localization signal peptide desirably functions to increase the secretion (i.e., the secretion potential) by a cell of (i) proteins (e.g., chimeric proteins) that are not normally secreted (i.e., secretable) by the cell and/or (ii) proteins (e.g., chimeric proteins) that are normally secreted by a cell, but in low (i.e., less than desired) quantities.

The ER localization signal peptide encoded by the polynucleotide can be any suitable ER localization signal peptide or polypeptide (i.e., protein). For example, the ER localization signal peptide encoded by the polynucleotide can be a peptide or polypeptide (i.e., protein) selected from the group consisting of nerve growth factor (NGF), immunoglobulin (Ig) (e.g., an Ig κ chain leader sequence), and midkine (MK), or a portion thereof. Suitable ER localization signal peptides also include those defined in Ladunga, "Large-scale predictions of secretory proteins from mammalian genomic and EST sequences," *Current Opinions in Biotechnology*, 11, 13–18 (2000). Moreover, the ER localization signal peptide can be any peptide or polypeptide (i.e., protein), many of which are known to those of ordinary skill in the art, that possesses the functional ability to direct DNA, RNA, and/or a protein to the membrane of the endoplasmic reticulum, wherein a protein is expressed and targeted for secretion.

The transport moiety encoded by the polynucleotide can be any suitable transport moiety. A "transport moiety" is defined herein as a molecule (e.g., protein) that has the functional ability to enter (i.e., become internalized or translocate) into any suitable cell and to carry (i.e., shuttle) other molecules (e.g., nucleic acids, peptides, polypeptides, and other small molecules) which are bound to the transport moiety (e.g., in the form of a chimeric protein or fusion protein) into the cell as well, such that the transport moiety and bound molecule become located in the cytosol and/or the nucleus of the cell. The transport moiety can shuttle into the cell one or more bound moieties of interest which are not normally internalized by the cell or which are normally internalized, but at less than desired concentrations.

Suitable transport moieties include, for example, moieties selected from the group consisting of human immunodeficiency virus transcriptional activation protein (HIV TAT), herpes simplex viral protein 22 (HSV VP22), lactoferrin, human T-cell leukemia virus translational trans-activator (HTLV Tax), fibroblast growth factor-1 (FGF-1), fibroblast growth factor-2 (FGF-2), Kaposi-FGF (i.e., K-FGF or FGF-4), the PreS2 domain of a hepatitis-B virus (HBV) surface antigen, a homeoprotein (e.g., the antennapedia protein, engrailed-1, engrailed-2, hoxa-5, hoxc-8, fushi tarazu, and transporting portions thereof, and combinations thereof), a penetratin, and transporting portions thereof, and combinations thereof. The transport moiety also can consist essentially of (a) the third helix region of a homeoprotein as disclosed, for example, in Prochiantz, "Homeodomain-derived Peptides," *Ann. NY Acad. Sci.*, 886, 172–179 (1999), (b) an amphipathic α-helix located between amino acids 41–52 of the PreS2 domain of an HBV surface antigen as disclosed, for example, in Oess et al., "Novel cell permeable motif derived from the PreS2-domain of hepatitis-B virus surface antigens," *Gene Therapy*, 7, 750–758 (2000), or (c) amino acids 49–59 of HIV TAT, as disclosed in U.S. Pat. No. 5,804,604 [SEQ ID NO:2], which is encoded by the nucleotide sequence of SEQ ID NO:1]. Preferably, the transport moiety is selected from the group consisting of HIV TAT, VP22, and the antennapedia protein.

The moiety of interest encoded by the polynucleotide can be any suitable moiety, e.g., any peptide, polypeptide, or protein (which terms are used synonymously herein), with any desired property, e.g., a diagnostic or therapeutic moiety. Moreover, a moiety of interest also can function as a transport moiety, e.g., HIV TAT. A moiety of interest is defined herein as one or more moieties (e.g., two or more moieties, three or more moieties, four or more moieties, or even five or more moieties). The moiety of interest desirably has a therapeutic effect on a cell or host containing the cell, i.e., desirably is a therapeutic moiety. Therapeutic effects include, for example, beneficial effects and/or deleterious effects on a cell into which the moiety of interest is internalized. In particular, a moiety of interest can be beneficial to a cell into which it is internalized if, for example, it replaces or supplements one or more proteins of the cell which are deficient in quantity or lacking altogether. In this regard, the beneficial moiety of interest can potentially restore normal functioning in a pathological cell. Moreover, a moiety of interest can be deleterious to a cell into which it is internalized if, for example, it inhibits a normal cell function (e.g., expression of a cellular protein) or if it is cytotoxic to the cell (e.g., induces the cell to undergo apoptosis). Accordingly, one of ordinary skill in the art will appreciate that any therapeutic moiety or other moiety of interest can be used in the context of the invention.

Suitable moieties of interest include, for example, enzymes (e.g., kinases), co-enzyme molecules, hormones, cytokines (e.g., lymphokines), receptors (e.g., cell surface receptors), mitogens (e.g., growth factors), regulatory factors (e.g., gene regulatory proteins), immunoglobulins, neuropeptides, neurotransmitters, antigen molecules, and active fragments of any of the foregoing (e.g., active domains thereof), and combinations thereof.

In this regard, suitable moieties of interest include, for example, anti-apoptotic moieties. An anti-apoptotic moiety is any biological factor that effects partial or complete prevention (i.e., inhibition) of apoptosis to achieve a therapeutic effect. Suitable anti-apoptotic moieties include, for example, viral caspase inhibitors, such as CrnA or the adenovirus 14.7K gene product, and mammalian caspase inhibitors, such as I-FLICE/FLIP, Bcl-2, Bcl-X$_L$, an adenoviral E1B product, and anti-apoptotic mutants thereof (e.g., dominant negative mutants thereof and dominant positive mutants thereof), anti-apoptotic fragments thereof (e.g., active domains thereof), and combinations thereof.

Suitable moieties of interest also include, for example, apoptotic, cytotoxic, and cytostatic moieties, such as, for example, caspases, protein kinases, transcription factors (e.g., transcriptional activators), signal transduction proteins, and mutants thereof (e.g., dominant negative mutants thereof and dominant positive mutants thereof), active fragments of any of the foregoing (e.g., active domains thereof), and combinations thereof. Preferably, the apoptotic, cytotoxic, and cytostatic moiety is selected from the group consisting of p53, Fas, Fas ligand, Fas-associating protein with death domain (FADD), caspase-3, caspase-8 (FLICE), caspase-10, Apo2L, tumor necrosis factor (TNF), TNF-R1, IκB, ΔIκB, receptor-interacting protein (RIP)-associated ICH-1/CED-3-homologous protein with a death domain (RAIDD), TNF-related apoptosis-inducing ligand (TRAIL), DR4, DR5, a cell death-inducing coding sequence of Bcl-2 which comprises an N-terminal deletion, a cell death-inducing coding sequence of Bcl-x which comprises an N-terminal deletion, Bax, Bak, Bid, Bad, Bik, Bif-2, c-myc, Ras, Raf, PCK kinase, AKT kinase, Akt/PI(3)-kinase, PITSLRE, death-associated protein (DAP) kinase, RIP, JNK/SAPK, Daxx, NIK, MEKK1, ASK1, PKR, and active mutants thereof (e.g., dominant negative mutants thereof and dominant positive mutants thereof), active fragments of any of the foregoing (e.g., active domains thereof), and combinations thereof.

Transcription factors that can be moieties of interest include, for example, E2F transcription factors and synthetic cell cycle-independent forms thereof, such as modified E2F1 transcription factors, as described, for example, in Cress et al., "Interacting domains of E2F1, DP1, and the Adenovirus E4 Protein," *Journal of Virology,* 68(7), 4212–4219 (1994), and E2F-VP transcription factors which contain the DNA binding and dimerization domains of E2F (i.e., amino acids 95–284), linked to the transactivation domain of VP16, and lacking a nuclear localization signal. Transcription factors that can be moieties of interest also include, for example, an AP1 transcription factor, an AP2 transcription factor, an SP transcription factor (e.g., an SP1 transcription factor), a helix-loop-helix transcription factor, a DP transcription factor (e.g., DP1, DP2, and DP3), and active mutants thereof (e.g., dominant negative mutants thereof and dominant positive mutants thereof), active fragments of any of the foregoing (e.g., active domains thereof), and combinations thereof. Moreover, transcription factors that can be moieties of interest include viral proteins, such as, for example, an adenoviral E1A product, an adenoviral E4/ORF6/7 product, an adenoviral E4/ORF4 product, a cytomegalovirus (CMV) product (e.g., CMV-thymidine kinase (CMV-TK)), a herpes simplex virus (HSV) product (e.g., HSV-TK), a human papillomavirus (HPV) product (e.g., HPVX), and active mutants thereof (e.g., dominant negative mutants thereof and dominant positive mutants thereof), active fragments of any of the foregoing (e.g., active domains thereof), and combinations thereof.

Suitable moieties of interest also include, for example, atonal-associated peptides, such as mouse atonal homolog-1 (Math-1), human atonal homolog-1 (Hath-1), or active fragments of either of the foregoing (e.g., biologically active fragments thereof), or a combination thereof. Math-1 is a member of the mouse basic helix-loop-helix family of transcription factors, as described, for example, in Birmingham et al., *Science,* 284, 1837–1841 (1999), and Zheng and Gao, *Nature Neuroscience,* 3(2), 580–586 (2000). Hath-1 is the human counterpart of Math-1.

The polynucleotide of the invention can further encode a nuclear localization signal (NLS). The NLS functions to direct the protein comprising the transport moiety and the moiety of interest, which is encoded by the polynucleotide, to the nucleus of a cell into which the protein is internalized (i.e., a different, generally neighboring, cell, referred to herein as a "secondary cell") after the protein is secreted from the cell into which the polynucleotide entered (i.e., the primary cell). In this regard, the protein comprising the transport moiety and the moiety of interest, which is encoded by the polynucleotide, is directed to (i.e., targets) either the nucleus of a secondary cell or the cytoplasm of a secondary cell, dependent on the presence, or lack thereof, respectively, of an NLS in the protein. The NLS can be any suitable NLS. For example, the NLS can be a simian virus 40 (SV40) large T antigen nuclear localization signal. Moreover, one of ordinary skill in the art will appreciate that the NLS can be any molecule (e.g., peptide or polypeptide) with the functional ability to target a cytosolic peptide or polypeptide for relocation to the nucleus of the cell. As is known to one of ordinary skill in the art, there are several sources of NLSs that function in this described manner.

Preferably, the polynucleotide of the invention further comprises a polyadenylation site following the coding region of the nucleotide sequence encoding the chimeric protein. Moreover, it is preferred that all of the proper transcription signals (and translation signals, where appropriate) are correctly arranged, such that the nucleotide sequence encoding the chimeric protein is properly expressed in the cell into which it is introduced. The nucleotide sequence of the polynucleotide also can comprise splice sites (i.e., splice acceptor and splice donor sites) to facilitate mRNA production. Moreover, the polynucleotide can comprise at least one nucleotide sequence that encodes at least one selectable marker that permits cells harboring the polynucleotide to be selected (e.g., the polynucleotide can encode resistance to antibiotics that kill cells not harboring the polynucleotide).

The polynucleotide of the invention can further comprise a promoter (i.e., a regulatory sequence). A promoter is defined herein as one or more promoters (e.g., two or more promoters, three or more promoters, four or more promoters, or even five or more promoters). A promoter is a DNA sequence that directs the binding of RNA polymerase and thereby promotes RNA synthesis and subsequent protein synthesis. Preferably, the polynucleotide comprises a promoter that is operably linked to a portion of the polynucleotide (i.e., a nucleotide sequence) that encodes and can be expressed to produce the chimeric protein comprising the ER localization signal peptide, the transport moiety, and the moiety of interest. A nucleotide sequence is operably linked to a promoter when the promoter is capable of directing transcription of that nucleotide sequence. A promoter can be native or non-native to the nucleotide sequence to which it is operably linked. Alternatively, the polynucleotide of the invention contains no promoter and undergoes site-specific recombination within a cell, as described, for example, in U.S. Pat. No. 5,801,030, such that a promoter is introduced into the polynucleotide, in such a manner that it is operably linked to a portion of the polynucleotide that encodes and can be expressed to produce the chimeric protein.

Any promoter (i.e., whether isolated from nature or produced by recombinant DNA or synthetic techniques) can be used in the context of the invention to provide for transcription of the nucleotide sequence. The promoter preferably is capable of directing transcription in a eukaryotic (desirably mammalian) cell.

The promoter of the polynucleotide desirably is a viral promoter. Suitable viral promoters are known in the art and include, for example, cytomegalovirus (CMV) promoters (e.g., a CMV immediate-early promoter), promoters derived from human immunodeficiency virus (HIV) (e.g., an HIV long terminal repeat promoter), Rous sarcoma virus (RSV) promoters (e.g., an RSV long terminal repeat promoter), an adenoviral promoter (e.g., the Ad2 or Ad5 major late promoter and tripartite leader), mouse mammary tumor virus (MMTV) promoters, HSV promoters (e.g., a herpes thymidine kinase promoter, as disclosed, for example, in Wagner et al., *Proc. Natl. Acad. Sci.*, 78, 144–145 (1981)), promoters derived from SV40 or Epstein Barr virus, and the like, and hybrids thereof (e.g., a CMV-RSV hybrid promoter).

Other suitable promoters for use in the invention include the regulatory sequences of the metallothionine gene (Brinster et al., *Nature*, 296, 39–42 (1982)), promoter elements from yeast or other fungi, such as the Gal 4 promoter, the alcohol dehydrogenase promoter, the phosphoglycerol kinase promoter, and the alkaline phosphatase promoter. Similarly, promoters isolated from the genomes of mammalian cells, such as the actin promoter (e.g., a human beta-actin promoter) or the muscle-creatine promoter, can be employed.

While the promoter can be a constitutive promoter, the promoter of the polynucleotide also can be a regulatable promoter, i.e., a promoter that is up-regulated and/or down-regulated in response to appropriate signals. For instance, the promoter can be inducible by at least one transcriptional activator (e.g., a cis-activator or a trans-activator) and/or repressible by at least one transcriptional repressor (e.g., a cis-repressor or a trans-repressor). A cis-regulator is defined herein as any suitable activator (i.e., cis-activator) or repressor (i.e., cis-repressor) encoded for by a portion of the polynucleotide of the invention. A trans-regulator is defined herein as any suitable activator (i.e., trans-activator) or repressor (i.e., trans-repressor) encoded for by a polynucleotide that is distinct from the polynucleotide of the invention. Moreover, the promoter can be inducible and/or repressible by an exogenous agent, such as, for example, a drug or an administered protein. It is also suitable for the promoter to be inducible and/or repressible by at least one molecule (e.g., protein) of a cell into which the polynucleotide of the invention is internalized (i.e., the primary cell). In this regard, the promoter can be a tissue-specific promoter, i.e., a promoter that is preferentially induced and/or repressed in a given tissue. In another embodiment, for example, the promoter of the polynucleotide of the invention is down-regulated (i.e., repressed) by at least one molecule (e.g., protein) within a producer cell of adenoviruses, such that expression of the polynucleotide is repressed, and such that the polynucleotide is packaged by the producer cell into an adenovirus. Examples of suitable regulatable promoter systems include, but are not limited to, the IL-8 promoter, the metallothionine inducible promoter system, the bacterial lacZYA expression system, the tetracycline expression system, a T7 polymerase system, a bipartite inducible system, and combinations thereof, as disclosed, for example, in Yao et al., *Human Gene Therapy*, 9, 1939–1950 (1998).

With respect to promoters, nucleotide sequences, selectable markers, and the like, located on the polynucleotide of the invention, such elements can be present as part of a cassette, either independently or coupled. In the context of the invention, a cassette is a particular nucleotide sequence that possesses functions which facilitate expression (e.g., polyadenylation or splice sites) of particular nucleotide sequences. The construction of the polynucleotide operably linked to one or more control regions, such as promoters, polyadenylation sites, and localization signal peptides, is well within the skill of the art. See, for example, Sambrook et al., *Molecular Cloning. A Laboratory Manual*, 2$^{nd}$ ed. (1989).

Specific constructs of the polynucleotide of the invention are illustrated in the Table below, which sets forth five non-limiting examples of constructs of the polynucleotide of the present invention. The constructs comprise a nucleotide sequence comprising (i) a promoter (specifically, a CMV promoter, an RSV promoter, or a human beta-actin promoter), (ii) an ER localization signal peptide (specifically, MK, NGF, or an Ig κ chain leader sequence), (iii) a transport moiety (specifically, HSV VP22 or HIV TAT), and (iv) a moiety of interest (specifically, FADD, an E2F-VP transcription factor, Hath-1, or CriA). Moreover, as indicated in the Table below, some constructs of the polynucleotide further comprise a nucleotide sequence encoding an NLS (specifically, an SV40 Large T antigen NLS).

TABLE

Exemplary Polynucleotide Constructs

| Polynucleotide Construct | Promoter | ER Localization Signal Peptide | Transport Moiety | Moiety of interest | NLS |
|---|---|---|---|---|---|
| A | CMV | MK | VP22 | FADD | None |
| B | CMV | NGF | HIV TAT | E2F-VP | SV40 Large T antigen NLS |
| C | RSV | MK | VP22 | Hath-1 | None |
| D | Human beta-actin | NGF | HIV TAT | CrmA | None |
| E | CMV | Ig κ chain leader sequence | HIV TAT | E2F-VP | SV40 Large T antigen NLS |

One of ordinary skill in the art will appreciate that any suitable vector can comprise the polynucleotide of the invention. For example, any suitable vector can comprise a first expression cassette comprising a polynucleotide as described herein operably linked to a regulatable promoter and a second expression cassette encoding a cis-regulator that regulates (e.g., modulates the expression of) the promoter of the first expression cassette. Alternatively, any suitable vector can be used in a regulatable expression system comprising (i) a first vector comprising a nucleotide sequence encoding a trans-regulator and (ii) a second vector comprising a polynucleotide as described herein operably linked to a regulatable promoter, wherein the trans-regulator regulates the promoter of the second vector.

Suitable expression vectors include, for instance, plasmids, plasmid-liposome complexes, and viral vectors, e.g., adeno-associated virus (AAV)-based vectors, retroviral vectors, herpes simplex virus (HSV)-based vectors, AAV-adenoviral chimeric vectors, and adenovirus-based vectors. Any of these polynucleotides can be prepared using standard recombinant DNA techniques described in, e.g., Sambrook et al., *Molecular Cloning: A Laboratory Manual*, 2$^{nd}$ ed. (1989), and Ausubel et al., *Current Protocols in Molecular Biology*, 1$^{st}$ ed. (1994).

Plasmids, genetically engineered circular double-stranded polynucleotides, can be designed to contain the polynucleotide as described herein. Although plasmids were the first vectors described for administration of therapeutic nucleotides, the efficiency of gene transfer achieved with plasmids alone is poor compared with other techniques. By complexing the plasmid with liposomes, the efficiency of gene transfer in general is improved. While the liposomes used for plasmid-mediated gene transfer strategies have various compositions, they are typically synthetic cationic lipids. Advantages of plasmid-liposome complexes include their ability to transfer large nucleotide sequences and their relatively low immunogenicity.

Plasmids are often used for short-term expression. However, a plasmid construct can be modified to obtain prolonged expression. It has recently been discovered that the inverted terminal repeats (ITR) of parvovirus, in particular adeno-associated virus (AAV), are responsible for the high-level persistent nucleotide expression often associated with AAV. Accordingly, the expression vector can be a plasmid comprising parvovirus ITRs to obtain prolonged and substantial expression of the polynucleotide of the invention. While plasmids are suitable for use in the context of the invention, preferably the expression vector is a viral vector.

AAV vectors are viral vectors of particular interest for use in gene therapy protocols. AAV is a DNA virus, which is not known to cause human disease. AAV requires co-infection with a helper virus (i.e., an adenovirus or a herpes virus), or expression of helper genes, for efficient replication. AAV vectors used for administration of a nucleotide sequence typically have approximately 96% of the parental genome deleted, such that only the terminal repeats (ITRs), which contain recognition signals for DNA replication and packaging, remain. This eliminates immunologic or toxic side effects due to expression of viral genes. In addition, delivering the AAV rep protein enables integration of the AAV vector comprising AAV ITRs into a specific region of genome, if desired. Although efficient, the need for helper virus or helper genes can be an obstacle for widespread use of this vector.

Retrovirus is an RNA virus that can infect a wide variety of host cells. Upon infection, the retroviral genome integrates into the genome of its host cell and is replicated along with host cell DNA, thereby constantly producing viral RNA and any nucleotide sequence incorporated into the retroviral genome. A retroviral vector can additionally be manipulated to render the virus replication-incompetent. As such, retroviral vectors are thought to be particularly useful for stable gene transfer in vivo. Lentiviral vectors, such as HIV-based vectors, are exemplary of retroviral vectors used for gene delivery.

HSV-based viral vectors also are suitable for use as expression vectors in the context of the invention. The mature HSV virion consists of an enveloped icosahedral capsid with a viral genome consisting of a linear double-stranded polynucleotide that is 152 kb. Most replication-deficient HSV vectors contain a deletion to remove one or more intermediate-early genes to prevent replication. Advantages of the herpes vector are its ability to enter a latent stage that can result in long-term DNA expression, and its large viral DNA genome that can accommodate exogenous DNA up to 25 kb. Of course, this ability is also a disadvantage in terms of short-term treatment regimens. For a description of HSV-based vectors appropriate for use in the context of the invention, see, for example, U.S. Pat. Nos. 5,837,532, 5,846,782, 5,849,572, and 5,804,413 and International Patent Applications WO 91/02788, WO 96/04394, WO 98/15637, and WO 99/06583.

Adenovirus (Ad) is a 36 kb double-stranded DNA virus that efficiently transfers nucleotide sequences (i.e., DNA) in vivo to a variety of different target cell types. The vector can be produced in high titers and can efficiently transfer DNA to replicating and non-replicating cells. The newly transferred genetic information remains epi-chromosomal, thus eliminating the risks of random insertional mutagenesis and permanent alteration of the genotype of the target cell. However, if desired, the integrative properties of AAV can be conferred to adenovirus by constructing an AAV-Ad chimeric vector. For example, the AAV ITRs and the nucleotide sequence encoding the Rep protein can be incorporated into an adenoviral vector to enable the adenoviral vector to integrate into a mammalian cell genome. The vector can be an adenoviral amplicon, e.g., an adenoviral amplicon comprising an ITR and any suitable origin of replication.

The adenoviral vector can be of any serotype of adenovirus, e.g., adenoviral serotypes 1 through 51, which are currently available from the American Type Culture Collection (ATCC, Manassas, Va.), or from any other serotype of adenovirus. For instance, the adenovirus can be of subgroup A (e.g., serotypes 12, 18, and 31), subgroup B (e.g., serotypes 3, 7, 11, 14, 16,21,34, and 35), subgroup C (e.g., serotypes 1, 2, 5, and 6), subgroup D (e.g., serotypes 8, 9, 10, 13, 15, 17, 19, 20, 22–30, 32, 33, 36–39, and 42–47), subgroup E (serotype 4), subgroup F (serotypes 40 and 41), or any other adenoviral serotype. Preferably, the adenovirus is of subgroup C, particularly of serotype 2 or 5. However, the adenovirus can be a non-group C adenovirus. Non-group C adenoviral vectors, methods of producing non-group C adenoviral vectors, and methods of using non-group C adenoviral vectors are disclosed in, for example, U.S. Pat. Nos. 5,801,030, 5,837,511, and 5,849, 561 and International Patent Applications WO 97/12986 and WO 98/53087.

The adenoviral vector desirably is deficient in at least one gene function (e.g., one, two, three, or more gene functions) required for viral replication (i.e., an essential gene function), thereby resulting in a replication-deficient adenoviral vector. Preferably, the adenoviral vector has at least one deficiency in one or more early regions of the adenoviral genome. For example, the adenoviral vector can be deficient in at least one essential gene function of the E1 or E4 region of the adenoviral genome (e.g., to form an E1$^-$ or E1$^-$E4$^-$ adenoviral vector). With respect to the E1 region, the adenoviral vector can be deficient in at least one essential gene function of the E1a region and/or at least one essential gene function of the E1b region (e.g., an E1a$^-$E1b$^-$ adenoviral vector). The E3 region of the adenoviral genome is not essential for viral replication, and an adenoviral vector can have an E3 region which has been deleted, in whole or in part, alone or in conjunction with essential gene function deficiencies (e.g., to form an E1E3$^-$ or E1a$^-$E1b$^-$E3$^-$ adenoviral vector). In addition, the adenoviral vector can have a mutation in the major late promoter (MLP). The mutation in the MLP can be in any of the MLP control elements such that it alters the responsiveness of the promoter, as discussed in International Patent Application WO 00/00628.

The adenoviral vector can be multiply deficient, meaning that the adenoviral vector is deficient in one or more essential gene functions required for viral replication in each of two or more regions, such as the E1 (e.g., E1a and/or E1b), E2 (e.g., E2a), and/or E4 regions, optionally in addition to a partial or complete deletion of the non-essential E3 region. For example, the aforementioned E1⁻ deficient or E1⁻, E3⁻ deficient adenoviral vectors can be further deficient in at least one essential gene function of the E4 region (e.g., to form an E1⁻E4⁻ or E1⁻E3⁻E4⁻ adenoviral vector). Alternatively, the adenoviral vector can be deficient in at least one essential gene function of the E1 and E2 regions (e.g., lacks all or part of the E1 region and all or part of the E2 region to form an E1⁻E2 adenoviral vector). Other suitable adenoviral vectors include adenoviral vectors, preferably replication-deficient adenoviral vectors, (a) lacking all or part of the E1 region, all or part of the E2 region, and all or part of the E3 region (i.e., E1⁻E2⁻E3⁻ adenoviral vectors), (b) lacking all or part of the E1 region, all or part of the E2 region, and all or part of the E4 region (i.e., E1⁻E2⁻E4 adenoviral vectors), and (c) lacking all or part of the E1 region, all or part of the E2 region, all or part of the E3 region, and all or part of the E4 region (i.e., E1⁻E2⁻E3⁻E4⁻ adenoviral vectors). Suitable replication-deficient adenoviral vectors are disclosed in U.S. Pat. Nos. 5,851,806 and 5,994,106 and International Patent Applications WO 95/34671 and WO 97/21826.

It also will be appreciated by one of ordinary skill in the art that the vector used in the context of the invention can comprise at least one modified coat protein. For example, the vector (e.g., adenoviral vector) can comprise at least one modified coat protein with lower or decreased immunogenicity (i.e., attraction to antibodies), as compared to wild-type coat proteins, as described, for example, in International Patent Application WO 98/40509. Moreover, the vector (e.g., adenoviral vector) can comprise at least one modified coat protein that increases the binding specificity of the vector for particular cells (e.g., desired target cells). For adenoviral vectors, increased binding specificity can be attained, for example, through deletions of at least one region of the fiber, penton, or hexon, and/or through insertions of various native or non-native ligands into portions of the coat protein, and the like. For example, the viral vector can comprise a chimeric coat protein (e.g., a fiber, hexon or penton protein), as described, for example, in International Patent Application WO 97/20051, which differs from the wild-type (i.e., native) coat protein by the introduction of at least one normative amino acid sequence, preferably at or near the carboxyl terminus. Preferably, the nonnative amino acid sequence is inserted into or in place of an internal coat protein sequence. The adenoviral vector also can comprise a short-shafted adenoviral fiber gene, as discussed in U.S. Pat. No. 5,962,311.

The ability of a vector (e.g., viral vector) to recognize a particular cell (e.g., target cell) can be modulated without modification or manipulation of the coat protein. For instance, complexing an adenovirus with a bispecific molecule comprising a penton base-binding domain and a domain that selectively binds a particular cell surface binding site enables the targeting of the vector to a particular cell type. Other suitable modifications to a viral vector, specifically an adenoviral vector, are described in U.S. Pat. Nos. 5,559,099, 5,731,190, 5,712,136, 5,770,442, 5,846,782, 5,926,311, and 5,965,541 and International Patent Applications WO 96/07734, WO 96/26281, WO 97/20051, WO 98/07865, WO 98/07877, and WO 98/54346.

It will be appreciated that numerous expression vectors are available commercially. Alternatively, expression vectors can be constructed in accordance with methods well-known in the art. Adenoviral vectors can be constructed and/or purified using the methods set forth, for example, in U.S. Pat. No. 5,965,358 and International Patent Applications WO 98/56937, WO 99/15686, and WO 99/54441.

The vector also can comprise matrix attachment region (MAR) sequences or locus control region (LCR) sequences. MAR sequences have been characterized as DNA sequences that associate with the nuclear matrix after a combination of nuclease digestion and extraction (Bode et al., *Science,* 255(5041), 195–197 (1992)). MAR sequences often are associated with enhancer-type regulatory regions, and, when integrated into genomic DNA, MAR sequences augment transcriptional activity of adjacent nucleotide sequences. It has been postulated that MAR sequences play a role in controlling the topological state of chromatin structures, thereby facilitating the formation of transcriptionally-active complexes. Similarly, it is believed LCR sequences function to establish and/or maintain domains permissive for transcription. Many LCR sequences give tissue specific expression of associated nucleotide sequences. Addition of MAR or LCR sequences to the polynucleotide can further enhance expression of the nucleotide sequence encoding the chimeric protein as described herein.

The invention also is directed to a cell comprising a polynucleotide, a vector, and/or a regulatable expression system as described herein. Moreover, the invention is directed to a cell line comprising a polynucleotide, a vector, and/or a regulatable expression system as described herein. A cell line is a population of cells established in culture, which bear common characteristics, e.g., cells that are genetically identical. A suitable cell line, for example, is a complementing cell line for propagation or growth of the vector of the invention (e.g., a replication deficient adenoviral vector), described, for example, in U.S. Pat. No. 5,851,806 and Brough et al., *Virol.,* 70, 6497–6501 (1996). In this regard, for example, the cell line can complement for at least one essential gene function of an adenoviral vector, e.g., the cell line can complement for the E1, E2, and/or E4 regions of an adenoviral vector genome when an adenoviral vector deficient in the essential gene functions of the E1, E2, and/or E4 regions is being utilized. The cell line can complement for other or all adenoviral functions. The cell line desirably contains the complementing genes in a manner that does not overlap the adenoviral vector genome, which minimizes, and practically eliminates, the possibility of the nucleotide sequence of the vector recombining with the cellular DNA. This eliminates the likelihood (e.g., possibility) of the creation of a replication-competent adenoviral vector that can replicate in non-complementing cells.

The cell and/or cell line of the invention can be produced by any suitable method. For example, a cell and/or a source cell line can be contacted with a polynucleotide, a vector, and/or regulatable expression system as described herein. In this regard, the invention also is directed to a method of expressing a protein, which method comprises contacting a cell (i.e., the primary cell), with the polynucleotide, the vector, and/or the regulatable expression system, as described herein, such that the polynucleotide, vector, and/or regulatable expression system enters the cell and is expressed to produce the chimeric protein, the ER localization signal peptide is cleaved from the chimeric protein, and a protein comprising the transport moiety and the moiety of interest is secreted from the cell (i.e., via an ER-dependent secretion pathway). Following secretion of the protein from the primary cell, the protein can be internalized by at least one secondary (i.e., different or neighboring) cell and can exert an effect, e.g., a therapeutic effect, on the secondary cell. The term "contacting" is defined herein as any manner by which the polynucleotide, vector, and/or regulatable expression system as described herein is brought into close proximity with a cell, or a group of cells (e.g., a cell line), desirably such that the polynucleotide, vector, and/or regulatable expression system enters the cell (e.g., by active transport or by passive transport across the cell membrane). For example, the polynucleotide, vector, and/or regulatable expression system can contact a cell (e.g., a universal donor cell), or a group of cells (e.g., a cell line), in vitro. The polynucleotide, vector, and/or regulatable expression system also can contact a cell, or a group of cells (e.g., a cell line), which have been explanted or removed from an animal (e.g., a human), ex vivo and then, optionally, the contacted cells can be administered either to the host animal from which the cell, or group of cells, was derived or to a different animal. Moreover, the polynucleotide, vector, and/or regulatable expression system can be administered to an animal, such that contact is made with a cell, or groups of cells, in vivo, preferably at a desired point of contact for internalization into the cell or group of cells (e.g., a particular organ, tissue, or tumor in the animal).

One skilled in the art will appreciate that suitable methods of contacting a cell, or groups of cells, in vitro or ex vivo with the polynucleotide, vector, and/or regulatable expression system of the invention are well-known and available through techniques which are commonly used in the art. Likewise, techniques for contacting a cell, or group of cells, in vivo with the polynucleotide, vector, and/or regulatable expression system of the invention also are well-known in the art, as disclosed, for example, in Rosenfeld et al., *Science*, 252, 431–434 (1991), Jaffe et al., *Clin. Res.*, 39(2), 302A (1991), Rosenfeld et al., *Clin. Res.*, 39(2), 311A (1991), and Berkner, *BioTechniques*, 6, 616–629 (1988).

A cell (i.e., a primary cell) can be contacted with a composition comprising the polynucleotide, vector, and/or regulatable expression system of the invention and a carrier, such as a pharmaceutically acceptable (e.g., a physiologically or pharmacologically acceptable) carrier (e.g., excipient or diluent). Suitable carriers are well-known to those of ordinary skill in the art and are readily available. The choice of carrier will be determined in part by the particular method used to contact a cell with the composition. Accordingly, there is a wide variety of suitable formulations of the composition for use in the context of the invention. The following formulations and methods are merely exemplary and are in no way limiting.

The polynucleotide, vector, and/or regulatable expression system of the invention, alone or in combination with a pharmaceutically acceptable carrier and/or other suitable components, can exist in a formulation suitable, for example, for oral administration, inhalation, parenteral administration, suppositories, or vaginal administration. In particular, formulations suitable for oral administration can be (a) liquid solutions, such as an effective amount of the active ingredient dissolved in diluents, such as water, saline, or orange juice, (b) capsules, sachets or tablets, each containing a predetermined amount of the active ingredient, as solids or granules, (c) suspensions in an appropriate liquid, and (d) suitable emulsions. Formulations suitable for aerosol formulations to be administered via inhalation include the active ingredient placed into pressurized acceptable propellants, such as dichlorodifluoromethane, propane, nitrogen, and the like, or formulated as non-pressurized preparations for use in a device such as a nebulizer or an atomizer. Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described. Formulations, suitable for suppositories, can be made by mixing the active ingredient with a variety of bases such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

The polynucleotide, vector, regulatable expression system, and/or composition in any suitable form can be delivered at any dosage appropriate to effect a desirable response, e.g., therapeutic or prophylactic response, within a desirable time frame. The proper dose in the context of the invention varies with the particular embodiment of the invention (e.g., the particular moiety of interest utilized, the particular vector utilized, and the desired therapeutic effect). The determination of suitable in vitro and ex vivo dosages can be determined by one of ordinary skill in the art by using standard methods that are readily available in the art. Suitable dosages for in vivo administration depend on factors, such as the type of organism being treated, characteristics of the host (e.g., individual) being treated (e.g., gender, age, body size, and sensitivity to treatment), the tissue to be treated, and the route of administration. Such a determination of a suitable dosage range is a common procedure, which is known and readily available to those of ordinary skill in the art. Suitable dosages can be measured, for example, on the scale of particle units (pu), also referred to as viral particles, wherein $1\times10^{12}$ pfu is equivalent to $1\times10^{14}$ pu.

The polynucleotide, vector, and/or regulatable expression system of the invention can be used to treat any cellular dysfunction, disease, or disorder that is due, at least in part, to an abnormality in one or more cellular nucleotides, polynucleotides, peptides, and/or polypeptides, such as, for example, an abnormality in protein structure, function, and/or expression (e.g., an overabundance or a deficiency in one or more cellular proteins). In this regard, the polynucleotide can be used to treat any disease or disorder for which therapeutic peptides and polypeptides (i.e., proteins) can potentially alleviate symptoms of the disease or disorder and/or produce some desired therapeutic effect.

The polynucleotide, vector, and/or regulatable expression system of the invention can be utilized to treat cancerous cells (e.g., a benign or malignant tumor) in an animal (e.g., a human). In this regard, for example, a moiety of interest of the polynucleotide of the invention can be an apoptotic moiety (e.g., E2F), as described above, and the polynucleotide, vector, and/or regulatable expression system of the invention can be administered in vivo to an animal (e.g., a human), wherein the polynucleotide, vector, and/or regulatable expression system exerts a therapeutic effect (i.e., an induction of apoptosis) on at least one secondary cell that is cancerous.

The polynucleotide, vector, and/or regulatable expression system of the invention also can be utilized to treat congenital, chronic, or acquired degenerative hearing impairments and/or loss or balance problems, e.g., deafness and vestibular disorders. For example, a moiety of interest of the polynucleotide of the present invention can be an atonal-associated peptide (e.g., Math-1 or Hath-1), as described above, and the polynucleotide, vector, and/or regulatable expression system of the invention can be administered in vivo to an animal (e.g., a human), wherein the polynucleotide, vector, and/or regulatable expression system exerts a therapeutic effect (e.g., an initiation of hair growth, such that the cell assumes the functions of a mechanoreceptor cell) on at least one secondary cell of the inner ear.

All of the references cited herein, including patents, patent applications, and publications, are hereby incorporated in their entireties by reference.

While this invention has been described with an emphasis upon preferred embodiments, variations of the preferred embodiments may be used, and it is intended that the invention may be practiced otherwise than as specifically described herein. Accordingly, this invention includes all modifications encompassed within the spirit and scope of the invention as defined by the claims.

herpes simplex viral protein 22, lactoferrin, human T-cell leukemia virus translational trans-activator, fibroblast growth factor-1, fibroblast growth factor-2, Kaposi-fibroblast growth factor, the PreS2 domain of a hepatitis-B virus surface antigen, a homeoprotein, a penetratin, and transporting portions thereof, and combinations thereof.

4. The polynucleotide of claim 1, wherein the moiety of interest is anti-apoptotic.

5. The polynucleotide of claim 1, wherein the moiety of interest is apoptotic, cytotoxic, or cytostatic.

6. The polynucleotide of claim 1, wherein the moiety of interest is selected from the group consisting of a caspase, a protein kinase, a transcriptional activator, a signal transduction protein, and combinations thereof.

7. The polynucleotide of claim 1, wherein the polynucleotide further comprises a promoter, which is operably linked to the portion of the polynucleotide encoding the chimeric protein.

8. A vector comprising the polynucleotide of claim 1.

9. The polynucleotide of claim 2, wherein the nuclear localization signal is a simian virus 40 large T antigen nuclear localization signal.

10. A vector comprising the polynucleotide of claim 2.

What is claimed is:

1. A polynucleotide encoding a chimeric protein comprising an endoplasmic reticulum localization signal peptide, a transport moiety, and a moiety of interest, wherein the endoplasmic reticulum localization signal peptide, the transport moiety, and the moiety of interest are operably linked to each other.

2. The polynucleotide of claim 1, wherein the polynucleotide further encodes a nuclear localization signal, which is operably linked to the endoplasmic reticulum localization signal peptide, the transport moiety, and the moiety of interest.

3. The polynucleotide of claim 1, wherein the transport moiety is selected from the group consisting of human immunodeficiency virus transcriptional activation protein, 11. The polynucleotide of claim 3, wherein the homeoprotein is selected from the group consisting of antennapedia, engrailed-1, engrailed-2, hoxa-5, hoxc-8, fushi tarazu, and transporting portions thereof, and combinations thereof.

12. The polynucleotide of claim 3, wherein the transport moiety consists essentially of the third helix region of a homeoprotein.

13. The polynucleotide of claim 3, wherein the transport moiety consists essentially of SEQ ID NO:2.

14. The polynucleotide of claim 7, wherein the promoter is a tissue-specific promoter.

15. The vector of claim 8, wherein the vector is a viral vector.

16. A cell comprising the vector of claim 8.

17. A method of producing a protein, which method comprises contacting a cell with the vector of claim 8, such that the polynucleotide enters the cell and is expressed to produce the chimeric protein, the endoplasmic reticulum localization signal peptide is cleaved from the chimeric protein, and a protein comprising the transport moiety and the moiety of interest is secreted from the cell.

18. The vector of claim 15, wherein the viral vector is an adenoviral vector.

19. The vector of claim 18, wherein the adenoviral vector is replication-deficient.

20. A cell comprising the vector of claim 10.

21. A method of producing a protein, which method comprises contacting a cell with the vector of claim 10, such that the polynucleotide enters the cell and is expressed to produce the chimeric protein, the endoplasmic reticulum localization signal peptide is cleaved from the chimeric protein, and a protein comprising the transport moiety and the moiety of interest is secreted from the cell.

22. The method of claim 17, wherein the protein that is secreted by the cell is internalized by a different cell.

23. The method of claim 22, wherein the protein exerts an effect on the different cell.

24. The method of claim 21, wherein the protein that is secreted by the cell is internalized by a different cell.

25. The method of claim 24, wherein the protein exerts an effect on the different cell.

\* \* \* \* \*

SEQUENCE LISTING

```
<160> NUMBER OF SEQ ID NOS: 2

<210> SEQ ID NO 1
<211> LENGTH: 33
<212> TYPE: DNA
<213> ORGANISM: Human immunodeficiency virus
<220> FEATURE:
<221> NAME/KEY: CDS
<222> LOCATION: (1)..(33)
<223> OTHER INFORMATION:

<400> SEQUENCE: 1 cgt aaa aaa cgt cgt cag cga cgt cgt ccg ccg                         33
Arg Lys Lys Arg Arg Gln Arg Arg Arg Pro Pro
1               5                   10

<210> SEQ ID NO 2
<211> LENGTH: 11
<212> TYPE: PRT
<213> ORGANISM: Human immunodeficiency virus

<400> SEQUENCE: 2

Arg Lys Lys Arg Arg Gln Arg Arg Arg Pro Pro
1               5                   10
```